United States Patent
Chan et al.

(10) Patent No.: US 10,099,978 B2
(45) Date of Patent: Oct. 16, 2018

(54) CATALYST AND METHOD FOR HYDROGENATION OF 1,3-CYCLOBUTANEDIKETONE COMPOUND

(71) Applicant: INDUSTRIAL TECHNOLOGY RESEARCH INSTITUTE, Hsinchu (TW)

(72) Inventors: Shu-Hua Chan, Zhuolan Township (TW); Hsi-Yen Hsu, Hsinchu (TW); Chiou-Hwang Lee, Hsinchu (TW); Ying-Chieh Lee, Taipei (TW)

(73) Assignee: INDUSTRIAL TECHNOLOGY RESEARCH INSTITUTE, Hsinchu (TW)

(*) Notice: Subject to any disclaimer, the term of this patent is extended or adjusted under 35 U.S.C. 154(b) by 0 days.

(21) Appl. No.: 15/598,923

(22) Filed: May 18, 2017

(65) Prior Publication Data

US 2017/0334815 A1    Nov. 23, 2017

Related U.S. Application Data

(60) Provisional application No. 62/338,689, filed on May 19, 2016.

(30) Foreign Application Priority Data

Apr. 7, 2017 (TW) .............................. 106111675 A
Apr. 27, 2017 (TW) .............................. 106114067 A

(51) Int. Cl.
*C07C 29/145* (2006.01)
*B01J 23/46* (2006.01)

(52) U.S. Cl.
CPC ........... *C07C 29/145* (2013.01); *B01J 23/462* (2013.01); *C07C 2601/04* (2017.05)

(58) Field of Classification Search
CPC .. C07C 2601/04; C07C 29/145; B01J 23/462; B01J 23/44; B01J 23/40
See application file for complete search history.

(56) References Cited

U.S. PATENT DOCUMENTS

| 2,936,324 | A | | 5/1960 | Hasek et al. |
| 4,910,180 | A | * | 3/1990 | Berndt ................. B01D 53/945 423/213.5 |
| 4,966,682 | A | | 10/1990 | Baird, Jr. et al. |
| 5,169,994 | A | | 12/1992 | Sumner, Jr. et al. |
| 5,900,386 | A | * | 5/1999 | Freund ..................... B01J 23/40 502/174 |
| 7,521,583 | B2 | | 4/2009 | McCusker-Orth et al. |
| 7,524,994 | B2 | | 4/2009 | McCusker-Orth et al. |
| 7,582,804 | B2 | | 9/2009 | McCusker-Orth et al. |
| 7,838,707 | B2 | | 11/2010 | McCusker-Orth et al. |
| 8,420,868 | B2 | * | 4/2013 | Liu ........................ C07C 29/145 568/839 |
| 8,722,922 | B2 | | 5/2014 | Chang et al. |
| 9,399,615 | B2 | | 7/2016 | Chen et al. |
| 2003/0036476 | A1 | * | 2/2003 | Arnold ..................... B01J 23/44 502/325 |
| 2006/0239893 | A1 | | 10/2006 | Zhang et al. |
| 2009/0283419 | A1 | * | 11/2009 | Del-Gallo .......... B01D 67/0046 205/628 |
| 2016/0158731 | A1 | | 6/2016 | Wu et al. |

FOREIGN PATENT DOCUMENTS

| CN | 1461746 | A | 12/2003 |
| CN | 1473072 | A | 2/2004 |
| CN | 103298774 | A | 9/2013 |
| TW | 201323397 | A | 6/2013 |
| TW | I534131 | B | 5/2016 |
| TW | 201620611 | A | 6/2016 |

OTHER PUBLICATIONS

Maciel, A.P., et al, "Chemical modification of the surface of alumina with alkaline earth metal oxides using the polymeric precursor method for catalysis application," Ceramica, 2014, vol. 60, pp. 154-159.
Taiwanese Office Action for Appl. No. 106114067 dated Dec. 6, 2017.
Cheng Guang-jian et al., "Synthesis technology and application status of 2,2,4,4, tetramethyl-1,3-cyclobutanediol", vol. 31, No. 4, Jul. 2013, pp. 342-346.
Edward U. Elam et al., "Chemistry of dimethylketene dimer. VII. Dimers of dimethylthioketene", The journal of organic Chemistry, Jan. 1, 1967, 32(5), pp. 1562-1565.
Li Yan et al., "Synthetic Methods of 2,2,4,4-Tetramethyl-1, 3-Cyclobutanedione", www.gdchem.comj, vol. 40, period 20, 2013, pp. 13-14.
Robert H. Hasek et al., "Chemistry of Dimethylketene Dimer. I. Catalytic Hydrogenation and Ring Cleavage by Alcohols", Hasek, Elam, Martin, and Nations, The Journal of organic Chemistry, Jan. 1, 1961, 26(3), pp. 700-704.
Thomas G. Osimitz et al., "Lack of androgenicity and estrogenicity of the three monomers used in Eastman's TritanTM copolyesters" Elsevier, Food and Chemical Toxicology, Jan. 1, 2012, (50), pp. 2196-2205.

* cited by examiner

*Primary Examiner* — Rosalynd A Keys
(74) *Attorney, Agent, or Firm* — Birch, Stewart, Kolasch & Birch, LLP

(57) ABSTRACT

Catalyst for hydrogenation of 1,3-cyclobutanediketone compound is provided, which includes a support and VIIIB group transition metal loaded thereon. The support includes a first oxide powder with a surface wrapped by a second oxide. The first oxide includes silicon oxide, aluminum oxide, zirconium oxide, titanium oxide, zinc oxide, or a combination thereof. The second oxide has a composition of $M_xAl_{(1-x)}O_{(3-x)/2}$, M is alkaline earth metal, and x is from 0.3 to 0.7.

16 Claims, No Drawings

CATALYST AND METHOD FOR HYDROGENATION OF 1,3-CYCLOBUTANEDIKETONE COMPOUND

CROSS REFERENCE TO RELATED APPLICATIONS

This application claims the benefit of U.S. Provisional Application No. 62/338,689 filed on May 19, 2016, priority of Taiwan Patent Application No. 106111675, filed on Apr. 7, 2017, and priority of Taiwan Paten Application No. 106114067, filed on Apr. 27, 2017, the entirety of which is incorporated by reference herein.

TECHNICAL FIELD

The technical field relates to hydrogenation, and it relates to catalyst for hydrogenation.

BACKGROUND 1,3-cyclobutanediol (CBDO) compound such as 2,2,4,4-tetramethyl-1,3-cyclobutanediol is a multi-functional intermediate, which is widely applied in the synthesis of copolyester. For example, the CBDO can be used to synthesize a high-performing polyester, and the polyester may replace polycarbonate. Conventional polyesters with a lower glass transition temperature are limited in the field of middle-temperature and high-temperature applications. Introduction of the CBDO may enhance the glass transition temperature, climate resistance, and transparency of the polyester. The polyester synthesized from the CBDO may have excellent physical properties (e.g. high impact strength and high glass transition temperature) as the polyester is synthesized from bisphenol A, but free of carcinogens and other toxic substances.

The major manufactures and the applications of the CBDO are developed by Eastman Company. The ketone groups of the tetramethyl-1,3-cyclobutanediketone are hydrogenated to alcohol groups by a high-pressure hydrogenation (e.g. reaction pressure of 100 bar) in Eastman hydrogenation process. However, the hydrogenation is performed at a higher temperature, such that the ring-opening side reactions occur easily. If the reaction pressure is reduced and the hydrogen/raw material ratio is increased to over 300, the conversion rate of the tetramethyl-1,3-cyclobutanediketone and the selectivity of the tetramethyl-1,3-cyclobutanediol can be increased. However, the reaction condition (e.g. the higher hydrogen/raw material ratio) will largely increase the cost of the hydrogen circle and industrial safety. Accordingly, a novel method and catalyst of hydrogenating the 1,3-cyclobutanediketone compound at a lower hydrogenation temperature and/or lower pressure is called for, which should simultaneously keep the high selectivity of the CBDO in the hydrogenation product.

SUMMARY

One embodiment of the disclosure provides a catalyst for hydrogenation of 1,3-cyclobutanediketone compound, comprising: a support including a first oxide powder with a surface wrapped by a second oxide; and VIIIB group transition metal loaded on the support, wherein the first oxide includes silicon oxide, aluminum oxide, zirconium oxide, titanium oxide, zinc oxide, or a combination thereof, and wherein the second oxide has a composition of $M_xAl_{(1-x)}O_{(3-x)/2}$, M is alkaline earth metal, and x is from 0.3 to 0.7.

One embodiment of the disclosure provides a method of hydrogenating of 1,3-cyclobutanediketone compound, comprising: hydrogenating 1,3-cyclobutanediketone compound by a catalyst and hydrogen to form 1,3-cyclobutanediol compound, wherein the catalyst for hydrogenation of 1,3-cyclobutanediketone compound includes: a support including a first oxide powder with a surface wrapped by a second oxide; and VIIIB group transition metal loaded on the support, wherein the first oxide includes silicon oxide, aluminum oxide, zirconium oxide, titanium oxide, zinc oxide, or a combination thereof, and wherein the second oxide has a composition of $M_xAl_{(1-x)}O_{(3-x)/2}$, M is alkaline earth metal, and x is from 0.3 to 0.7.

A detailed description is given in the following embodiments.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details.

In one embodiment of the disclosure, a catalyst for hydrogenation of 1,3-cyclobutanediketone compound is provided, which includes a support and VIIIB group transition metal loaded thereon. In one embodiment, the VIIIB group transition metal includes ruthenium, palladium, or a combination thereof. The support includes a first oxide powder with a surface wrapped by a second oxide. The first oxide includes silicon oxide, aluminum oxide, zirconium oxide, titanium oxide, zinc oxide, or a combination thereof. In one embodiment, the first oxide can be a porous support with a specific surface area of 100 $m^2/g$ to 300 $m^2/g$. In general, the greater specific surface area is beneficial to the reaction. The second oxide has a composition of $M_xAl_{(1-x)}O_{(3-x)/2}$, M is alkaline earth metal, and x is from 0.3 to 0.7. In one embodiment, the x is from 0.4 to 0.6. In one embodiment, the alkaline earth metal M includes magnesium, calcium, or a combination thereof.

In one embodiment, the first oxide and the second oxide in the support have a weight ratio of 1:3 to 4:1. In one embodiment, the first oxide and the second oxide in the support have a weight ratio of 1.5:1 to 3:1. The x value (M content ratio) of the second oxide composition and the weight ratio of the first oxide/second oxide relates to the properties (e.g. pH value) of the support. In general, the pH value of the support is increased by enhancing the x value and the second oxide ratio. Appropriate x value and second oxide ratio (equal to the M content ratio in the support) may increase the reactivity and the selectivity of the desired product. In one embodiment, the M salt and the aluminum salt can be dissolved in an alkaline solution to form M-Al sol-gel. Subsequently, the M-aluminum sol-gel and the first oxide are mixed, filtered, sintered, baked to be dried, and crushed to obtain the support. The support includes the first oxide with a surface wrapped by the second oxide (M-aluminum oxide).

In one embodiment, the VIIIB group transition metal and the support have a weight ratio of 1:10 to 1:200. In one embodiment, the VIIIB group transition metal and the support have a weight ratio of 1:10 to 1:50. Too much the VIIIB group transition metal may increase the catalyst cost. Too little the VIIIB group transition metal may not efficiently hydrogenating the 1,3-cyclobutanediketone. In one embodiment, the support may further include rare earth element, and the rare earth element occupies 1 wt % to 10 wt % of the support, wherein the rare earth element includes lanthanum, cerium, or a combination thereof.

In one embodiment, the support of the catalyst includes the porous aluminum oxide powder (optionally including lanthanum oxide) wrapped by magnesium aluminum oxide. The ruthenium metal is loaded on the support.

In one embodiment, the support further includes a forming agent therein. For example, the forming agent can be alumina sol, silica sol, titanium sol, zirconium sol, or pitch. The forming agent functions to mold the support of the catalyst as a desired shape (e.g. column-shaped).

In one embodiment, the catalyst is collocated with hydrogen to hydrogenate the 1,3-cyclobutanediketone for forming 1,3-cyclobutanediol. When the 1,3-cyclobutanediketone diketone compound has a chemical structure of

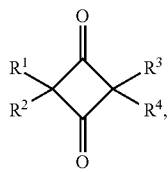

the hydrogenated product 1,3-cyclobutanediol compound has a chemical structure of

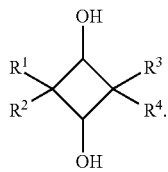

When the 1,3-cyclo-butanediketone compound has a chemical structure of

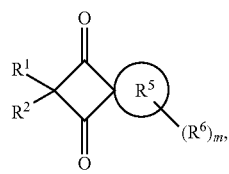

the hydrogenated product 1,3-cyclobutanediol compound has a chemical structure of

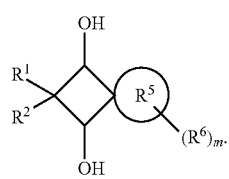

When the 1,3-cyclobutanediketone compound has a chemical structure of

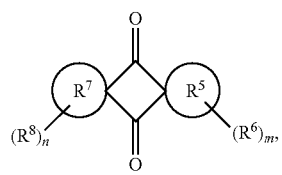

the hydrogenated product 1,3-cyclobutanediol compound has a chemical structure of

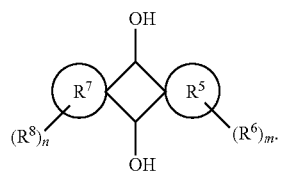

Each of $R^1$, $R^2$, $R^3$, and $R^4$ is independently H, $C_{1-10}$ alkyl group, $C_{5-10}$ cycloalkyl group, or $C_{6-10}$ aryl group. Each of $R^5$ and $R^7$ is independently $C_{5-10}$ cycloalkyl group. Each of $R^6$ and $R^8$ is independently H, $C_{1-10}$ alkyl group, $C_{5-10}$ cycloalkyl group, or $C_{6-10}$ aryl group. Each of n and m is independently from 4 to 9. In one embodiment, the 1,3-cyclobutanediketone compound has a chemical structure of

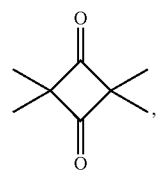

and the 1,3-cyclobutanediol compound has a chemical structure of

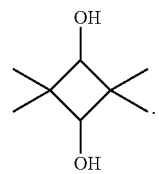

In one embodiment, the 1,3-cyclobutanediketone compound has a chemical structure of

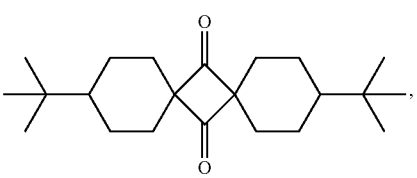 [SMILES: CC(C)(C)C1CCC2(CC1)C(=O)C1(CCC(C(C)(C)C)CC1)C2=O]

and the 1,3-cyclobutanediol compound has a chemical structure of

In one embodiment, the 1,3-cyclobutanediketone compound has a chemical structure of

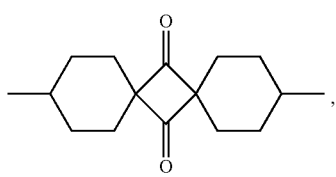

and the 1,3-cyclobutanediol compound has a chemical structure of

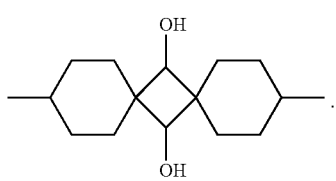

In one embodiment, the 1,3-cyclobutanediketone compound has a chemical structure of

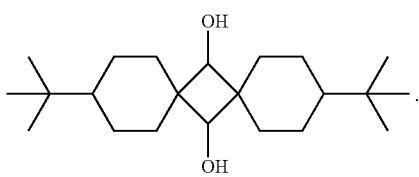

and the 1,3-cyclobutanediol compound has a chemical structure of

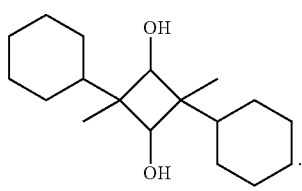 [SMILES: CC1(C2CCCCC2)C(O)C(C)(C2CCCCC2)C1O]

In one embodiment, the 1,3-cyclobutanediketone compound has a chemical structure of

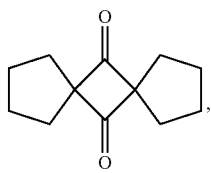 [SMILES: O=C1C2(CCCC2)C(=O)C12CCCC2]

and the 1,3-cyclobutanediol compound has a chemical structure of

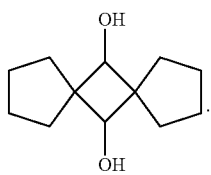 [SMILES: OC1C2(CCCC2)C(O)C12CCCC2]

In one embodiment, the 1,3-cyclobutanediketone compound has a chemical structure of

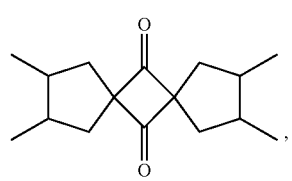

and the 1,3-cyclobutanediol compound has a chemical structure of

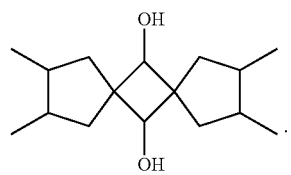

In addition to the above 1,3-cyclobutanediketone compounds, other 1,3-cyclobutanediketone compounds can be selected to form corresponding 1,3-cyclobutanediol compounds.

In one embodiment, the hydrogen pressure of the hydrogenation can be from 10 bar to 120 bar. In one embodiment, the hydrogen pressure of the hydrogenation can be from 30 bar to 70 bar. In general, the hydrogenation rate is increased by increasing the hydrogen pressure. However, an overly high hydrogen pressure may increase the cost of equipment and industrial safety. In one embodiment, the hydrogenation can be performed at a temperature of 50° C. to 200° C. In one embodiment, the hydrogenation can be performed at a temperature of 60° C. to 120° C. The hydrogenation rate is increased by increasing the temperature, but an overly high temperature of the hydrogenation may increase a side product ratio.

The hydrogenation of the 1,3-cyclobutanediketone compound utilizing the catalyst has specific results, such as (1) hydrogenation under middle and low temperature and middle pressure, (2) conversion rate over 99%, and (3) high selectivity of the 1,3-cyclobutanediol compound in the products.

Below, exemplary embodiments will be described in detail so as to be easily realized by a person having ordinary knowledge in the art. The inventive concept may be embodied in various forms without being limited to the exemplary embodiments set forth herein. Descriptions of well-known parts are omitted for clarity.

EXAMPLES

Preparation Example A

1 L of an aqueous solution of de-ionized water containing 256 g of magnesium nitrate and 357 g of aluminum nitrate was added to 1 L of another aqueous solution of de-ionized water containing 208 g of sodium hydroxide and 152 g of sodium carbonate, and then stirred at room temperature to be aged for 18 hours to form a magnesium aluminum sol-gel. 200 g of aluminum oxide powder (composed of 95 wt % of aluminum oxide and 5 wt % of lanthanum oxide) was then added to the magnesium aluminum sol-gel, continuously stirred for 1 hour, and filtered to obtain a filtered cake. The filtered cake was washed with water 3 times, and then dried at 110° C. The dried powder (aluminum oxide/lanthanum oxide powder with a surface wrapped by magnesium aluminum oxide) was molded to form particles with a uniform mesh of 20 to 30, and the particles would serve as a support to load catalyst. 20 g of the support was added into an $RuCl_3$ solution (containing 0.4 g of ruthenium) and stirred for 20 minutes to be evenly dispersed, then heated to 120° C. and kept at 120° C. for 5 hours to remove the solvent, then heated to 200° C. and sintered at 200° C. for 12 hours, then put into water of 80° C. to be washed 5 times, and then dried at 120° C. for 4 hours, thereby obtaining a catalyst A. The catalyst A included the support with a surface covered by ruthenium, and the support and the ruthenium had a weight ratio of 100:2.

Preparation Example B 20 g of aluminum oxide ($Al_2O_3$) was added into an $RuCl_3$ solution (containing 0.4 g of ruthenium) and stirred for 20 minutes to be evenly dispersed, then heated to 120° C. and kept at 120° C. for 5 hours to remove the solvent, then heated to 200° C. and sintered at 200° C. for 12 hours, then put into water of 80° C. to be washed 5 times, and then dried at 120° C. for 4 hours, thereby obtaining a catalyst B. The catalyst B included the aluminum oxide support with a surface covered by ruthenium, and the aluminum oxide and the ruthenium had a weight ratio of 100:2.

Preparation Example C 20 g of zeolite (ZSM-5 commercially available from sud-chemie, $SiO_2/AL_2O_3$=27) was added into an $RuCl_3$ solution (containing 0.4 g of ruthenium) and stirred for 20 minutes to be evenly dispersed, then heated to 120° C. and kept at 120° C. for 5 hours to remove the solvent, then heated to 200° C. and sintered at 200° C. for 12 hours, then put into water of 80° C. to be washed 5 times, and then dried at 120° C. for 4 hours, thereby obtaining a catalyst C. The catalyst C included the zeolite support with a surface covered by ruthenium, and the zeolite and the ruthenium had a weight ratio of 100:2.

Preparation Example D

1 L of an aqueous solution of de-ionized water containing 256 g of magnesium nitrate and 357 g of aluminum nitrate was added to 1 L of another aqueous solution of de-ionized water containing 208 g of sodium hydroxide and 152 g of sodium carbonate, and then stirred at room temperature to be aged for 18 hours to form a magnesium aluminum sol-gel. 100 g of aluminum oxide powder (composed of 95 wt % of aluminum oxide and 5 wt % of lanthanum oxide) was then added to the magnesium aluminum sol-gel, continuously stirred for 1 hour, and filtered to obtain a filtered cake. The filtered cake was washed with water 3 times, and then dried at 110° C. The dried powder (aluminum oxide/lanthanum oxide powder with a surface wrapped by magnesium aluminum oxide) was molded to form particles with a uniform mesh of 20 to 30, and the particles would serve as a support to load catalyst. 20 g of the support was added into an $RuCl_3$ solution (containing 1.6 g of ruthenium) and stirred for 20 minutes to be evenly dispersed, then heated to 120° C. and kept at 120° C. for 5 hours to remove the solvent, then heated to 200° C. and sintered at 200° C. for 12 hours, then put into water of 80° C. to be washed 5 times, and then dried at 120° C. for 4 hours, thereby obtaining a catalyst D. The catalyst D included the support with a surface covered by ruthenium, and the support and the ruthenium had a weight ratio of 100:8.

Preparation Example E

1 L of an aqueous solution of de-ionized water containing 256 g of magnesium nitrate and 357 g of aluminum nitrate was added to 1 L of another aqueous solution of de-ionized water containing 208 g of sodium hydroxide and 152 g of sodium carbonate, and then stirred at room temperature to be aged for 18 hours to form a magnesium aluminum sol-gel. 100 g of aluminum oxide powder (composed of >99 wt % of aluminum oxide) was then added to the magnesium aluminum sol-gel, continuously stirred for 1 hour, and filtered to obtain a filtered cake. The filtered cake was washed with water 3 times, and then dried at 110° C. The dried powder (aluminum oxide powder with a surface wrapped by magnesium aluminum oxide) was molded to form particles with a uniform mesh of 20 to 30, and the particles would serve as a support to load catalyst. 20 g of the support was added into an $RuCl_3$ solution (containing 0.4 g of ruthenium) and stirred for 20 minutes to be evenly dispersed, then heated to 120° C. and kept at 120° C. for 5 hours to remove the solvent, then heated to 200° C. and sintered at 200° C. for 12 hours, then put into water of 80° C. to be washed 5 times, and then dried at 120° C. for 4 hours, thereby obtaining a catalyst E. The catalyst E included the support with a surface covered by ruthenium, and the support and the ruthenium had a weight ratio of 100:2.

Preparation Example F

1 L of an aqueous solution of de-ionized water containing 256 g of magnesium nitrate and 357 g of aluminum nitrate was added to 1 L of another aqueous solution of de-ionized water containing 208 g of sodium hydroxide and 152 g of sodium carbonate, and then stirred at room temperature to be aged for 18 hours to form a magnesium aluminum sol-gel. 100 g of aluminum oxide powder (composed of >99 wt % of aluminum oxide) was then added to the magnesium aluminum sol-gel, continuously stirred for 1 hour, and filtered to obtain a filtered cake. The filtered cake was washed with water 3 times, and then dried at 110° C. The dried powder (aluminum oxide powder with a surface wrapped by magnesium aluminum oxide) was molded to form particles with a uniform mesh of 20 to 30, and the particles would serve as a support to load catalyst. 20 g of the support was added into an RuCl₃ solution (containing 1.6 g of ruthenium) and stirred for 20 minutes to be evenly dispersed, then heated to 120° C. and kept at 120° C. for 5 hours to remove the solvent, then heated to 200° C. and sintered at 200° C. for 12 hours, then put into water of 80° C. to be washed 5 times, and then dried at 120° C. for 4 hours, thereby obtaining a catalyst F. The catalyst F included the support with a surface covered by ruthenium, and the support and the ruthenium had a weight ratio of 100:8.

Example 1

6 mL of the catalyst A (20 to 30 mesh) was put into a fixed bed reactor and tested in a continuous trickle-bed mode. 4 wt % of 2,2,4,4-tetramethyl-1,3-cyclobutanediketone was hydrogenated in the above reactor with hydrogen. The hydrogenation factors are listed below: the solvent was ethyl acetate (EA), the weight hourly space velocity (WHSV) of the feed was 0.24 hr⁻¹, the hydrogenation temperature was 80° C., the hydrogenation pressure was 35 kg/cm², in which the hydrogen and the 2,2,4,4-tetramethyl-1,3-cyclobutanediketone had a molar ratio of 69. The hydrogenation result was analyzed by gas chromatography (GC) as indicated below: the conversion rate of the 2,2,4,4-tetramethyl-1,3-cyclobutanediketone was 99.9%, and the selectivity of the 2,2,4,4-tetramethyl-1,3-cyclobutanediol (CBDO) in the products was 77.6%, as shown in Table 1.

Example 2

Example 2 was similar to Example 1, except that the reaction pressure was changed to 60 kg/cm², in which the hydrogen and the 2,2,4,4-tetramethyl-1,3-cyclobutanediketone had a molar ratio of 69. The other reaction factors in Example 2 were similar to those in Example 1. The hydrogenation result was analyzed by GC as indicated below: the conversion rate of the 2,2,4,4-tetramethyl-1,3-cyclobutanediketone was 99.9%, and the selectivity of the CBDO in the products was 98.4%, as shown in Table 2.

Example 3

6 mL of the catalyst B (20 to 30 mesh) was put into a fixed bed reactor and tested in a continuous trickle-bed mode. 4 wt % of 2,2,4,4-tetramethyl-1,3-cyclobutanediketone was hydrogenated in the above reactor with hydrogen. The hydrogenation factors are listed below: the solvent was EA, the WHSV of the feed was 0.24 hr⁻¹, the hydrogenation temperature was 80° C., the hydrogenation pressure was 35 kg/cm², in which the hydrogen and the 2,2,4,4-tetramethyl-1,3-cyclobutanediketone had a molar ratio of 69. The hydrogenation result was analyzed by GC as indicated below: the conversion rate of the 2,2,4,4-tetramethyl-1,3-cyclobutanediketone was 88.6%, and the selectivity of the CBDO in the products was 7.4%, as shown in Table 1.

Example 4

Example 4 was similar to Example 3, except that the reaction pressure was changed to 60 kg/cm², in which the hydrogen and the 2,2,4,4-tetramethyl-1,3-cyclobutanediketone had a molar ratio of 69. The other reaction factors in Example 4 were similar to those in Example 3. The hydrogenation result was analyzed by GC as indicated below: the conversion rate of the 2,2,4,4-tetramethyl-1,3-cyclobutanediketone was 99.9%, and the selectivity of the CBDO in the products was 20.6%, as shown in Table 2.

Example 5

6 mL of the catalyst C (20 to 30 mesh) was put into a fixed bed reactor and tested in a continuous trickle-bed mode. 4 wt % of 2,2,4,4-tetramethyl-1,3-cyclobutanediketone was hydrogenated in the above reactor with hydrogen. The hydrogenation factors are listed below: the solvent was EA, the WHSV of the feed was 0.24 hr⁻¹, the hydrogenation temperature was 80° C., the hydrogenation pressure was 35 kg/cm², in which the hydrogen and the 2,2,4,4-tetramethyl-1,3-cyclobutanediketone had a molar ratio of 69. The hydrogenation result was analyzed by GC as indicated below: the conversion rate of the 2,2,4,4-tetramethyl-1,3-cyclobutanediketone was 61.8%, and the selectivity of the CBDO in the products was 1.7%, as shown in Table 1.

Example 6

Example 6 was similar to Example 5, except that the reaction pressure was changed to 60 kg/cm², in which the hydrogen and the 2,2,4,4-tetramethyl-1,3-cyclobutanediketone had a molar ratio of 69. The other reaction factors in Example 6 were similar to those in Example 5. The hydrogenation result was analyzed by GC as indicated below: the conversion rate of the 2,2,4,4-tetramethyl-1,3-cyclobutanediketone was 99.4%, and the selectivity of the CBDO in the products was 22.7%, as shown in Table 2.

TABLE 1

| | | (reaction pressure of 35 bar) | | | |
| --- | --- | --- | --- | --- | --- |
| Example | Catalyst type | Conversion rate Selectivity(%) | CBDO Selectivity(%) | Cyclic ketol Selectivity(%) | Ring-opening side products Selectivity(%) |
| Example 1 | Catalyst A (self-made support) | 99.9 | 77.6 | 21.9 | 0.5 |
| Example 3 | Catalyst B (Al₂O₃ support) | 88.6 | 7.4 | 88.7 | 3.9 |
| Example 5 | Catalyst C (zeolite support) | 61.8 | 1.7 | 62.3 | 36 |

As shown in Table 1, the self-made catalyst (with the support containing magnesium aluminum oxide) had the best conversion rate of 2,2,4,4-tetramethyl-1,3-cyclobutanediketone, the best selectivity of the CBDO in the products, and the lower ring-opening side products than those of the catalysts with the Al₂O₃ support and the zeolite support.

The partially hydrogenated cyclic ketol product could be separated and recycled. The cyclic ketol had a chemical structure of

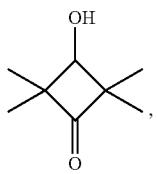

and the ring-opening side products included ring-opening ketol such as

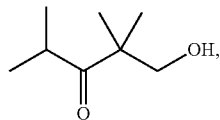

TMPD such as

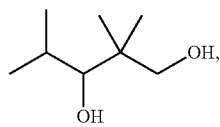

DIPK such as

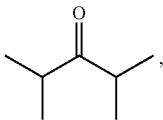

DIPA such as

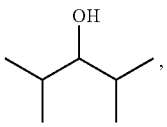

or a combination thereof best conversion rate of 2,2,4,4-tetramethyl-1,3-cyclobutanediketone, the best selectivity of the CBDO in the products, and the lower ring-opening side products than those of the catalysts with the $Al_2O_3$ support and the zeolite support. As shown in Tables 1 and 2, increasing the hydrogen pressure could increase the selectivity of the CBDO in the products. The definitions of the cyclic ketol and the ring-opening side products are shown above.

Example 7-1

6 mL of the catalyst D (20 to 30 mesh) was put into a fixed bed reactor and tested in a continuous trickle-bed mode. 4 wt % of 2,2,4,4-tetramethyl-1,3-cyclobutanediketone was hydrogenated in the above reactor with hydrogen. The hydrogenation factors are listed below: the solvent was n-butanol (BuOH), the WHSV of the feed was 0.24 $hr^{-1}$, the liquid hourly space velocity (LHSV) of the feed was 4 $hr^{-1}$, the hydrogenation temperature was 135° C., the hydrogenation pressure was 50 kg/cm², in which the hydrogen and the 2,2,4,4-tetramethyl-1,3-cyclobutanediketone had a molar ratio of 69. The hydrogenation result was analyzed by gas chromatography (GC) as indicated below: the conversion rate of the 2,2,4,4-tetramethyl-1,3-cyclobutanediketone was 99.8%, and the selectivity of the CBDO in the products was 10%, as shown in Table 3.

Example 7-2

Example 7-2 was similar to Example 7-1, except that the reaction pressure was changed to 35 kg/cm², in which the hydrogen and the 2,2,4,4-tetramethyl-1,3-cyclobutanediketone had a molar ratio of 69, the WHSV of the feed being lowered to 0.12 $hr^{-1}$, the LHSV of the feed being lowered to 2 $hr^{-1}$, and the reaction temperature being lowered to 100° C. The other reaction factors in Example 7-2 were similar to those in Example 7-1. The hydrogenation result was analyzed by GC as indicated below: the conversion rate of the 2,2,4,4-tetramethyl-1,3-cyclobutanediketone was 99.9%, and the selectivity of the CBDO in the products was 77.3%, as shown in Table 3.

Example 7-3

Example 7-3 was similar to Example 7-2, except that the reaction temperature was lowered to 80° C. The other reaction factors in Example 7-3 were similar to those in Example 7-2. The hydrogenation result was analyzed by GC as indicated below: the conversion rate of the 2,2,4,4-tetramethyl-1,3-cyclobutanediketone was 99.9%, and the

TABLE 2

| | | (reaction pressure of 60 bar) | | | |
|---|---|---|---|---|---|
| Example | Catalyst type | Conversion rate (%) | CBDO Selectivity(%) | Cyclic ketol Selectivity(%) | Ring-opening side products Selectivity(%) |
| Example 2 | Catalyst A (self-made support) | 99.9 | 98.4 | 1.5 | 0.1 |
| Example 4 | Catalyst B ($Al_2O_3$ support) | 99.9 | 20.6 | 77.8 | 1.6 |
| Example 6 | Catalyst C (zeolite support) | 99.4 | 22.7 | 73.5 | 3.8 |

As shown in Table 2, the self-made catalyst (with the support containing magnesium aluminum oxide) had the selectivity of the CBDO in the products was 97.2%, as shown in Table 3.

TABLE 3

(catalyst D)

| Example | Temperature °C. | Pressure bar | WHSV h$^{-1}$ | LHSV h$^{-1}$ | Conversion rate % | Selectivity (%) | | | | | |
|---|---|---|---|---|---|---|---|---|---|---|---|
| | | | | | | CBDO | Cyclic ketol | Ring-opening ketol | TMPD | DIPK | DIPA |
| 7-1 | 135 | 50 | 0.24 | 4 | 99.8 | 10 | 0 | 22 | 17.2 | 1.9 | 48.7 |
| 7-2 | 100 | 35 | 0.12 | 2 | 99.9 | 77.3 | 0 | 17.3 | 2.8 | 0.4 | 0.3 |
| 7-3 | 80 | 35 | 0.12 | 2 | 99.9 | 97.2 | 0 | 2.1 | 0.2 | 0 | 0 |

As shown in Table 3, when the catalyst D with a higher Ru ratio was adopted, lowering the hydrogenation temperature could enhance the selectivity of the CBDO in the products without reducing the conversion rate of 2,2,4,4-tetramethyl-1,3-cyclobutanediketone.

Example 8

Example 8 was similar to Example 1, except that the reaction pressure was changed to 20 kg/cm$^2$, in which the hydrogen and the 2,2,4,4-tetramethyl-1,3-cyclobutanediketone had a molar ratio of 69. The other reaction factors in Example 8 were similar to those in Example 1. The hydrogenation result was analyzed by GC as indicated below: the conversion rate of the 2,2,4,4-tetramethyl-1,3-cyclobutanediketone was 99.9%, and the selectivity of the CBDO in the products was 76.3%, as shown in Table 4.

TABLE 4

(catalyst A)

| Example | Temperature °C. | Pressure bar | WHSV h$^{-1}$ | LHSV h$^{-1}$ | Conversion rate % | Selectivity (%) | | | | | |
|---|---|---|---|---|---|---|---|---|---|---|---|
| | | | | | | CBDO | Cyclic ketol | Ring-opening ketol | TMPD | DIPK | DIPA |
| 2 | 80 | 60 | 0.24 | 4 | 99.9 | 98.4 | 1.5 | 0.08 | 0 | 0 | 0 |
| 1 | 80 | 35 | 0.24 | 4 | 99.9 | 77.6 | 21.9 | 0.2 | 0 | 0.3 | 0 |
| 8 | 80 | 20 | 0.24 | 4 | 99.9 | 76.3 | 23.1 | 0.3 | 0 | 0 | 0 |

As shown in Table 4, increasing the hydrogenation pressure could increase the selectivity of the CBDO in the products. As shown in Tables 3 and 4, increasing the Ru content in the catalyst could increase the selectivity of the CBDO in the products.

Example 8-1

6 mL of the catalyst E (20 to 30 mesh) was put into a fixed bed reactor and tested in a continuous trickle-bed mode. 4 wt % of 2,2,4,4-tetramethyl-1,3-cyclobutanediketone was hydrogenated in the above reactor with hydrogen. The hydrogenation factors are listed below: the solvent was EA, the WHSV of the feed was 0.24 hr$^{-1}$, the LHSV of the feed was 4 hr$^{-1}$, the hydrogenation temperature was 80° C., the hydrogenation pressure was 35 kg/cm$^2$, in which the hydrogen and the 2,2,4,4-tetramethyl-1,3-cyclobutanediketone had a molar ratio of 69. The hydrogenation result was analyzed by gas chromatography (GC) as indicated below: the conversion rate of the 2,2,4,4-tetramethyl-1,3-cyclobutanediketone was 99.9%, and the selectivity of the CBDO in the products was 99.2%, as shown in Table 5. On the other hand, after the continuous hydrogenation was performed over 135 hours, the conversion rate of the 2,2,4,4-tetramethyl-1,3-cyclobutanediketone was 99.9%, and the selectivity of the CBDO in the products was 99.5%. Obviously, the catalyst and the hydrogenation factors had a long-term stability.

Example 8-2

Example 8-2 was similar to Example 8-1, except that the reaction temperature was lowered to 70° C. The other reaction factors in Example 8-2 were similar to those in Example 8-1. The hydrogenation result was analyzed by GC as indicated below: the conversion rate of the 2,2,4,4-tetramethyl-1,3-cyclobutanediketone was 99.95%, the selectivity of the CBDO in the products was 92.8%, and the ring-opening side products ratio was very low, as shown in Table 5.

Example 8-3

Example 8-3 was similar to Example 8-1, except that the reaction temperature was lowered to 60° C. The other reaction factors in Example 8-3 were similar to those in Example 8-1. The hydrogenation result was analyzed by GC as indicated below: the conversion rate of the 2,2,4,4-tetramethyl-1,3-cyclobutanediketone was 99.18%, the selectivity of the CBDO in the products was 75.2%, as shown in Table 5.

Example 8-4

Example 8-4 was similar to Example 8-1, except that the reaction temperature was lowered to 60° C., and the reaction pressured was increased to 60 kg/cm$^2$, in which the hydrogen and the 2,2,4,4-tetramethyl-1,3-cyclobutanediketone had a molar ratio of 69. The other reaction factors in Example 8-4 were similar to those in Example 8-1. The hydrogenation result was analyzed by GC as indicated below: the conversion rate of the 2,2,4,4-tetramethyl-1,3-cyclobutanediketone was 99.9%, the selectivity of the CBDO in the products was 99.2%, as shown in Table 5.

TABLE 5

| Example | Catalyst | Temperature °C. | Pressure bar | WHSV h$^{-1}$ | LHSV h$^{-1}$ | Conversion rate % | Selectivity (%) | | | | | |
|---|---|---|---|---|---|---|---|---|---|---|---|---|
| | | | | | | | CBDO | Cyclic ketol | Ring-opening ketol | TMPD | DIPK | DIPA |
| 1 | A (with La) | 80 | 35 | 0.24 | 4 | 99.9 | 77.6 | 21.9 | 0.2 | 0 | 0.3 | 0 |
| 8-1 | E (no La) | 80 | 35 | 0.24 | 4 | 99.9 | 99.2 | 0.21 | 0.15 | 0.06 | 0 | 0 |
| 8-2 | E (no La) | 70 | 35 | 0.24 | 4 | 99.9 | 92.8 | 6.9 | 0.26 | 0.04 | 0 | 0 |
| 8-3 | E (no La) | 60 | 35 | 0.24 | 4 | 99.2 | 75.2 | 24.5 | 0.29 | 0.04 | 0 | 0 |
| 8-4 | E (no La) | 60 | 60 | 0.24 | 4 | 99.9 | 99.2 | 0.56 | 0.14 | 0.06 | 0 | 0 |

As shown in Table 5, the selectivity of the CBDO would be also excellent even if the support was free of La. On the other hand, lowering the hydrogenation temperature could lower the selectivity of the CBDO in the products, but the reaction pressure could be increased to collocate the lower temperature for enhancing the selectivity of the CBDO in the products.

Example 9-1

6 mL of the catalyst F (20 to 30 mesh) was put into a fixed bed reactor and tested in a continuous trickle-bed mode. 4 wt % of 2,2,4,4-tetramethyl-1,3-cyclobutanediketone was hydrogenated in the above reactor with hydrogen. The hydrogenation factors are listed below: the solvent was EA, the WHSV of the feed was 0.24 hr$^{-1}$, the LHSV of the feed was 4.5 hr$^{-1}$, the hydrogenation temperature was 60° C., the hydrogenation pressure was 20 kg/cm$^2$, in which the hydrogen and the 2,2,4,4-tetramethyl-1,3-cyclobutanediketone had a molar ratio of 69. The hydrogenation result was analyzed by GC as indicated below: the conversion rate of the 2,2,4,4-tetramethyl-1,3-cyclobutanediketone was 99.9%, and the selectivity of the CBDO in the products was 99.6%, as shown in Table 6.

Example 9-2

Example 9-2 was similar to Example 9-1, except that the 2,2,4,4-tetramethyl-1,3-cyclobutanediketone concentration was changed to 6 wt % and the LHSV of the feed was lowered to 3 hr$^{-1}$. The other reaction factors in Example 9-2 were similar to those in Example 9-1. The hydrogenation result was analyzed by GC as indicated below: the conversion rate of the 2,2,4,4-tetramethyl-1,3-cyclobutanediketone was 99.9%, and the selectivity of the CBDO in the products was 99.3%, as shown in Table 6.

Example 9-3

Example 9-3 was similar to Example 9-1, except that the 2,2,4,4-tetramethyl-1,3-cyclobutanediketone concentration was changed to 8 wt % and the LHSV of the feed was lowered to 2.25 hr$^{-1}$. The other reaction factors in Example 9-3 were similar to those in Example 9-1. The hydrogenation result was analyzed by GC as indicated below: the conversion rate of the 2,2,4,4-tetramethyl-1,3-cyclobutanediketone was 99.9%, and the selectivity of the CBDO in the products was 99.1%, as shown in Table 6.

Example 9-4

Example 9-4 was similar to Example 9-3, except that the solvent was changed to a co-solvent of EA and BuOH (weight ratio of 0.5:0.5). The other reaction factors in Example 9-4 were similar to those in Example 9-3. The hydrogenation result was analyzed by GC as indicated below: the conversion rate of the 2,2,4,4-tetramethyl-1,3-cyclobutanediketone was 99.9%, the selectivity of the CBDO in the products was 93.8%, and the ring-opening side products ratio was low, as shown in Table 6.

Example 9-5

Example 9-5 was similar to Example 9-4, except that the 2,2,4,4-tetramethyl-1,3-cyclobutanediketone concentration was changed to 10 wt % and the LHSV of the feed was lowered to 1.8 hr$^{-1}$. The other reaction factors in Example 9-5 were similar to those in Example 9-4. The hydrogenation result was analyzed by GC as indicated below: the conversion rate of the 2,2,4,4-tetramethyl-1,3-cyclobutanediketone was 99.9%, the selectivity of the CBDO in the products was 93.5%, and the ring-opening side products ratio was low, as shown in Table 6.

Example 9-6

Example 9-6 was similar to Example 9-5, except that the reaction pressure was increased to 60 kg/cm$^2$, in which the hydrogen and the 2,2,4,4-tetramethyl-1,3-cyclobutanediketone had a molar ratio of 69. The other reaction factors in Example 9-6 were similar to those in Example 9-5. The hydrogenation result was analyzed by GC as indicated below: the conversion rate of the 2,2,4,4-tetramethyl-1,3-cyclobutanediketone was 99.9%, the selectivity of the CBDO in the products was 99.5%, as shown in Table 6.

TABLE 6

| Example | catalyst | Ru wt. % | Reactant concentration wt % | EA:BuOH wt | Pressure bar | WHSV h$^{-1}$ | LHSV h$^{-1}$ | Conversion rate % | Selectivity (%) | | | | | |
|---|---|---|---|---|---|---|---|---|---|---|---|---|---|---|
| | | | | | | | | | CBDO | Cyclic ketol | Ring-opening ketol | TMPD | DIPK | DIPA |
| 8-4 | E | 2 | 4 | 1:0 | 60 | 0.24 | 4 | 99.9 | 99.2 | 0.56 | 0.14 | 0.06 | 0 | 0 |
| 9-1 | F | 8 | 4 | 1:0 | 20 | 0.24 | 4.5 | 99.9 | 99.6 | 0.41 | 0 | 0 | 0 | 0 |
| 9-2 | F | 8 | 6 | 1:0 | 20 | 0.24 | 3 | 99.9 | 99.3 | 0.66 | 0.04 | 0 | 0 | 0 |
| 9-3 | F | 8 | 8 | 1:0 | 20 | 0.24 | 2.25 | 99.9 | 99.1 | 0.85 | 0.05 | 0 | 0 | 0 |

TABLE 6-continued

| Example | catalyst | Ru wt. % | Reactant concentration wt % | EA:BuOH wt | Pressure bar | WHSV h$^{-1}$ | LHSV h$^{-1}$ | Conversion rate % | Selectivity (%) | | | | | |
|---|---|---|---|---|---|---|---|---|---|---|---|---|---|---|
| | | | | | | | | | CBDO | Cyclic ketol | Ring-opening ketol | TMPD | DIPK | DIPA |
| 9-4 | F | 8 | 8 | 0.5:0.5 | 20 | 0.24 | 2.25 | 99.9 | 93.8 | 5.10 | 0.04 | 0 | 0 | 0 |
| 9-5 | F | 8 | 10 | 0.5:0.5 | 20 | 0.24 | 1.8 | 99.9 | 93.5 | 5.4 | 0.05 | 0 | 0 | 0 |
| 9-6 | F | 8 | 10 | 0.5:0.5 | 60 | 0.24 | 1.8 | 99.9 | 99.5 | 0.4 | 0.05 | 0 | 0 | 0 |

As shown in Table 6, when the catalyst F with a higher Ru ratio was selected, lowering the hydrogenation pressure would not lower the selectivity of the CBDO in the products. On the other hand, the hydrogenation may collocate with different solvent types, different reactant concentrations, and different feed flow rates to enhance the process flexibility of the hydrogenation.

Example 10

7 mL of the catalyst E (20 to 30 mesh) was put into a fixed bed reactor of ½ inch and tested in a continuous trickle-bed mode. 4 wt % of 2,2,4,4-tetramethyl-1,3-cyclobutanediketone was hydrogenated in the above reactor with hydrogen. The hydrogenation factors are listed below: the solvent was EA, the WHSV of the feed was 0.24 hr$^{-1}$, the hydrogenation temperature was 80° C., the hydrogenation pressure was 60 kg/cm$^2$, in which the hydrogen and the 2,2,4,4-tetramethyl-1,3-cyclobutanediketone had a molar ratio of 12. The hydrogenation result was analyzed by GC as indicated below: the conversion rate of the 2,2,4,4-tetramethyl-1,3-cyclobutanediketone was 99.9%, and the selectivity of the CBDO in the products was 99.1%.

It will be apparent to those skilled in the art that various modifications and variations can be made to the disclosed methods and materials. It is intended that the specification and examples be considered as exemplary only, with the true scope of the disclosure being indicated by the following claims and their equivalents.

What is claimed is:

1. A catalyst for hydrogenation of 1,3-cyclobutanediketone compound, comprising:
  a support including a first oxide powder with a surface wrapped by a second oxide; and
  VIIIB group transition metal loaded on the support,
  wherein the first oxide includes silicon oxide, aluminum oxide, zirconium oxide, titanium oxide, zinc oxide, or a combination thereof, and
  wherein the second oxide has a composition of M$_x$Al$_{(1-x)}$O$_{(3-x)/2}$, M is alkaline earth metal, and x is from 0.4 to 0.7.

2. The catalyst as claimed in claim 1, wherein the alkaline earth metal comprises magnesium, calcium, or a combination thereof.

3. The catalyst as claimed in claim 1, wherein the VIIIB group transition metal comprises ruthenium, palladium, or a combination thereof.

4. The catalyst as claimed in claim 1, wherein the first oxide and the second oxide have a weight ratio of 1:3 to 4:1.

5. The catalyst as claimed in claim 1, wherein the VIIIB group transition metal and the support have a weight ratio of 1:10 to 1:200.

6. The catalyst as claimed in claim 1, wherein the support further comprises a rare earth metal, and the rare metal earth metal occupies 1 wt % to 10 wt % of the support.

7. A method of hydrogenating of 1,3-cyclobutanediketone compound, comprising:
  hydrogenating 1,3-cyclobutanediketone compound by a catalyst and hydrogen to form 1,3-cyclobutanediol compound,
  wherein the catalyst for hydrogenation of 1,3-cyclobutanediketone compound includes:
  a support including a first oxide powder with a surface wrapped by a second oxide; and
  VIIIB group transition metal loaded on the support,
  wherein the first oxide includes silicon oxide, aluminum oxide, zirconium oxide, titanium oxide, zinc oxide, or a combination thereof, and
  wherein the second oxide has a composition of M$_x$Al$_{(1-x)}$O$_{(3-x)/2}$, M is alkaline earth metal, and x is from 0.4 to 0.7.

8. The method as claimed in claim 7, wherein the alkaline earth metal comprises magnesium, calcium, or a combination thereof.

9. The method as claimed in claim 7, wherein the VIIIB group transition metal comprises ruthenium, palladium, or a combination thereof.

10. The method as claimed in claim 7, wherein the first oxide and the second oxide have a weight ratio of 1:3 to 4:1.

11. The method as claimed in claim 7, wherein the VIIIB group transition metal and the support have a weight ratio of 1:10 to 1:200.

12. The method as claimed in claim 7, wherein the support further comprises a rare earth metal, and the rare metal earth metal occupies 1 wt % to 10 wt % of the support.

13. The method as claimed in claim 7, wherein the 1,3-cyclobutanediketone compound has a chemical structure of:

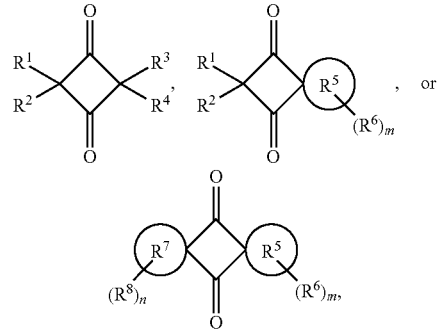

wherein each of R$^1$, R$^2$, R$^3$, and R$^4$ is independently H, C$_{1-10}$ alkyl group, C$_{5-10}$ cycloalkyl group, or C$_{6-10}$ aryl group,
each of R$^5$ and R$^7$ is independently C$_{5-10}$ cycloalkyl group,
each of R$^6$ and R$^8$ is independently H, C$_{1-10}$ alkyl group, C$_{5-10}$ cycloalkyl group, or C$_{6-10}$ aryl group, and
each of n and m is independently from 4 to 9.

14. The method as claimed in claim 7, wherein the 1,3-cyclobutanediol compound has a chemical structure of:

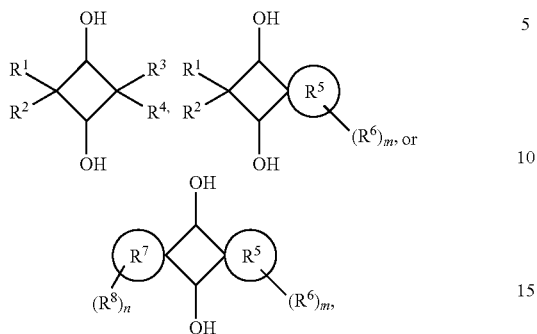

wherein each of $R^1$, $R^2$, $R^3$, and $R^4$ is independently H, $C_{1-10}$ alkyl group, $C_{5-10}$ cycloalkyl group, or $C_{6-10}$ aryl group, each of $R^5$ and $R^7$ is independently $C_{5-10}$ cycloalkyl group, each of $R^6$ and $R^8$ is independently H, $C_{1-10}$ alkyl group, $C_{5-10}$ cycloalkyl group, or $C_{6-10}$ aryl group, and each of n and m is independently from 4 to 9.

15. The method as claimed in claim 7, wherein a pressure of the hydrogen is from 10 bar to 120 bar.

16. The method as claimed in claim 7, wherein the step of hydrogenating 1,3-cyclobutanediketone compound is performed at a temperature of 50° C. to 200° C.

* * * * *